United States Patent [19]

Barrett

[11] Patent Number: 4,608,021
[45] Date of Patent: Aug. 26, 1986

[54] METHOD AND APPARATUS FOR DENTAL RESTORATION USING LIGHT CURABLE RESTORATIVES

[76] Inventor: Ronald A. Barrett, 4616 S. Green Acres Ct., Metairie, La. 70003

[21] Appl. No.: 766,939

[22] Filed: Aug. 19, 1985

[51] Int. Cl.$^4$ ............................................. A61C 5/04
[52] U.S. Cl. ...................................... 433/229; 433/215
[58] Field of Search ........................ 433/155, 229, 215

[56] References Cited

U.S. PATENT DOCUMENTS 4,553,936 11/1985 Wang .................................. 433/229
4,557,693 12/1985 Ellggren ............................ 433/229

*Primary Examiner*—Robert Peshock
*Attorney, Agent, or Firm*—Ziems, Walter & Shannon

[57] ABSTRACT

A method and apparatus for restoration of teeth using light curable restoratives while assuring interproximal contact between the restored tooth and an adjacent tooth. The apparatus is in the form of a triangle-like block defining two arms converging at a common point and which are of a different length. The longer of the two arms is provided with a camming surface on the end thereof opposite from the common pointed edge whereas the shorter of the two arms is provided with an abutment surface on the end thereof opposite from the common pointed edge. A tooth cavitation opening through a vertical tooth surface about which a matrix band has been tightened is filled by alternate deposition and curing of successive layers of the light curable restorative to a level at or below the plane of the maximum circumference of the tooth. The block is placed with the shorter arm against the top of the previously cured filling with the abutment surface against the matrix band so that a ledge of cured restorative may be built about the pointed end of the block. Thereafter, the block is removed and reinserted with the longer leg down and operable as a camming strut pivotable about the previously formed step or ledge against the matrix band to deform it outwardly for subsequent filling and curing of the restorative.

8 Claims, 9 Drawing Figures

METHOD AND APPARATUS FOR DENTAL RESTORATION USING LIGHT CURABLE RESTORATIVES

BACKGROUND OF THE INVENTION

This invention relates to restoration of teeth. More particularly, it concerns a method and apparatus especially, but not exclusively, adapted to the restoration of posterior teeth using light curable, polymeric restoratives while assuring proximal contact of the restored tooth with an adjacent tooth.

In the restoration of posterior teeth by forming and filling a cavity opening through front and/or rear vertical surfaces of a tooth, it is conventional practice to tighten a deformable, foil-like matrix band about the vertical tooth surfaces to form a dam across the open vertical mouth of the cavity. In the past, metallic amalgams have been used almost exclusively to fill such cavities primarily because of the facility they provide for compaction into the cavity. The compactability of the amalgam filling is important not only to the avoidance of air spaces in the restorative filling but also to deformation of the matrix band out to the original contour of the vertical tooth surface through which the cavity was opened. Such deformation of the matrix band under compacting forces exerted on the restorative amalgam is necessary to achieve proximal contact of the restored tooth with an adjacent tooth, a condition which exists with normal healthy teeth, particularly posterior teeth or molars.

While metallic amalgams have been used extensively and successfully for many years in the restoration of posterior teeth, resin based restoratives, particularly light curable polymeric restoratives, have become increasably popular in recent years primarily because of the conformity of such materials in color and surface texture to natural teeth enamels. Also the resin materials can be securely bonded to the cavity surfaces of the restoed tooth. Typically, resin-based restoratives are built up in layers within a cavity to be filled, each layer being cured or hardened by exposure to actinic light near the ultraviolet end of the visible light spectrum. Once the cavity is filled by alternate deposition and curing of successive layers, the outer surfaces of the restorative are finished to the exterior tooth contour in conventional fashion.

A major difficulty in the use of light curable, resin-based restoratives, particularly in the restoration of posterior teeth or molars where interproximal contact is considered essential, is that the uncured polymeric material is in the nature of a viscous liquid or of a plastic consistency. As a result, the uncured material tends to flow around conventional compacting tools rather than to transmit the compacting force of the tool laterally against the tightened matrix band. Because the tightened matrix band establishes a chord-like dam across the vertical opening of the tooth cavity to be filled, the cured resin restorative tends to assume the same configuration as the tightened matrix band to effect a flattened interproximal surface on the restored tooth which does not make good contact with an adjacent tooth. While the light curable restorative compositions have been developed to improve their "packability", the basically plastic nature of the uncured resin falls substantially short of the measure of matrix band deformation attainable by compaction of amalgam restoratives. Accordingly, there is a need for improvement in the attainment of interproximal contact between a tooth restored with light curable polymeric materials and an adjacent tooth.

SUMMARY OF THE PRESENT INVENTION

In accordance with the present invention, a method and apparatus is provided for the restoration of teeth using light curable, polymeric restorative compositions while providing for deformation of a tightened matrix band outwardly to a configuration approximating the original tooth contour using a prop-like camming device in the cavity. The camming device is shaped to facilitate its use with minimal interference to depositing the uncured polymer restorative into the cavity and with substantially no interference to light curing of the deposited polymer.

The camming device is a generally triangular-shaped block adaptable to molding or other formation in various sizes and having a pair of different length arms which converge at a common pointed edge. The shorter of the two arms serves as a gauge block for establishing a ledge or step of cured polymer restorative in the cavity spaced inwardly from the matrix band. The longer arm serves as a matrix band expanding strut with the point of the block anchored in the ledge or step of cured restorative. Additional uncured restorative may be placed about the device while it holds the band. By making the block from transparent materials such as polycarbonate, the block presents no interference with light curing of the subsequently deposited restorative.

In using the camming device to restore a cavitated tooth about which a matrix band has been tightened, the lower portion of the cavity may be filled with successively cured layers in conventional fashion. When the filling proceeds to a level near the plane of maximum circumference of the tooth, the device is placed, with the short arm or side down, and extending from the matrix band with the point of the device located within the cavity and spaced from the band by the length of the short arm. Light curable restorative composition is then placed and cured about the device to form a step formation at the point of the device. The camming device is then inverted to place the long arm or strut down but with the point against abutting the step previously formed. Because of the length of the longer arm, it will be inclined as a camming strut between the step and the matrix band. As such, the device is operable to force the band outwardly by cam action when the outer end thereof is depressed forceably into the cavity. The edge of the device lying between the short and long arms may be notched so that the short arm portion thereof serves as a handle for gripping by tweezers or the like.

Accordingly, it is a principal object of the present invention to provide a method and apparatus for tooth restoration using light curable polymeric restoratives and in the manner to enable the attainment of proximal contact of the restored tooth with an adjacent tooth. Other objects and further scope of applicability of the present invention will become apparent from the detailed description to follow taken in conjunction with the accompanying drawings in which like parts are designated by like reference numerals.

DETAILED DESCRIPTION OF THE PREFERRED EMBODIMENTS

Figure 1:
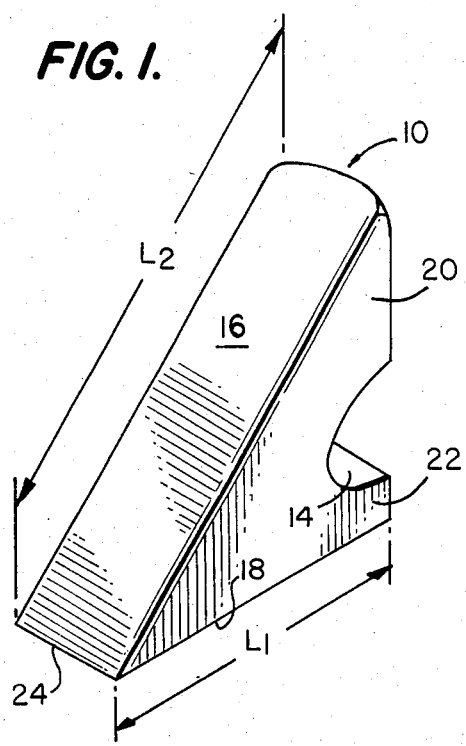
FIG. 1 is an enlarged isometric view illustrating an embodiment of the device of the present invention.
Figure 1A:
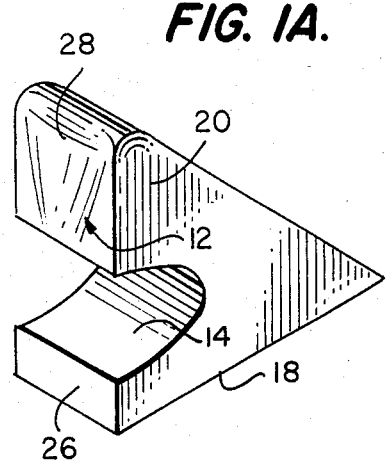
FIG. 1A is a similar view of the same embodiment from the opposite end thereof.

In FIGS. 1 and 1A of the drawings, an embodiment of the apparatus of the present invention is represented by a wedge-shaped block generally designated by the reference numeral 10 and illustrated at a greatly enlarged scale. In side elevation, the block 10 is generally triangular in configuration with one side 12 having a notch 14 so that the other two sides 16 and 18 respectively delineate with the notch 14, two arm portions 20 and 22 converging at a pointed edge 24. The arm 22 terminates at the end thereof opposite from the pointed edge 24 in a planar abutment face 26 which is parallel to the pointed edge 24 and perpendicular to the side 18. The length of the arm 22 between the pointed edge 24 and abutment face 26 is designated by the dimension $L_1$ in FIG. 1.

The end of the arm 20 opposite from the pointed edge 24 is preferably defined by a bulbous or convexly rounded camming surface 28 for reasons which will become more apparent from the detailed description of the use of the device 10 to follow. It is to be noted, however, that the length of the arm 20 between the pointed edge 24 and the camming surface 28, or the dimension $L_2$ in FIG. 1, is longer than the dimension $L_1$ as a result of the side surface 16 in the illustrated embodiment lying on the hypotenuse of the right-triangular configuration of the block 10.

The block 10 illustrated in FIGS. 1 and 1A is of uniform thickness throughout and as such may be cut, if desired, from plate stock material. Also as will become apparent from the use of the device in the description to follow, it is advantageous that the block 10 be formed from transparent material such as polycarbonate or other transparent plastics having comparable physical characteristics.

A more complete understanding of structural parameters incident to use of the block 10 may be had by reference to FIGS. 4–8 of the drawings in which successive stages of tooth restoration, using the present invention, are depicted. Thus, in FIGS. 4 and 5, a molar 30 to be restored is conventionally prepared by drilling to remove decayed portions and to form a shaped cavitation 32. The cavitation 32, in this instance, opens through the front vertical or mesial surface 34 of the molar which is proximal to an adjacent tooth 36. A matrix band 38 is then placed about the cavitated molar 30 and tightened using a clamp 40 only partially illustrated in FIG. 4. Such clamps are well known in the art and operate to place the matrix band 38 in hoop stressed tension about the tooth. Also it is common practice in the placement of matrix bands to forceably separate the tooth to be restored from an adjacent tooth either to facilitate placement of the band between the tooth under restoration and an adjacent tooth, to develop proximal contact of the restored tooth with an adjacent tooth after the band has been removed or for both of these purposes. In this respect, one or more wedges or toothpicks 41 may be used to separate the tooth 30 from the tooth 36.

Once in place, the matrix band 38 assumes an upwardly diverging, generally frusto-conical configuration about the tooth 30 to which it has been applied and forms a dam-like closure 39 across the vertical opening of the cavitation 32. It will be noted, however, that that portion 39 of the band 38 which spans the vertical opening of the cavitation is drawn to a chord across the edges of the cavitation to establish a relatively flat conformation across the cavitation and in which the spacing of the band portion from the adjacent tooth 36 is increased from the original rounded mesial surface. Thus, if the tooth 30 is to be in proximal contact with the adjacent tooth 36 after restoration, the process of filling the cavitation 32 must be associated with a deflection of the band 30 out to the original or natural contour of the molar 30. In the past, the filling of posterior teeth or molars with metallic amalgams has been justified by the ability of such materials, upon compaction, to force the matrix band outwardly toward an adjacent tooth or the tooth 36, in this instance.

Figure 6:
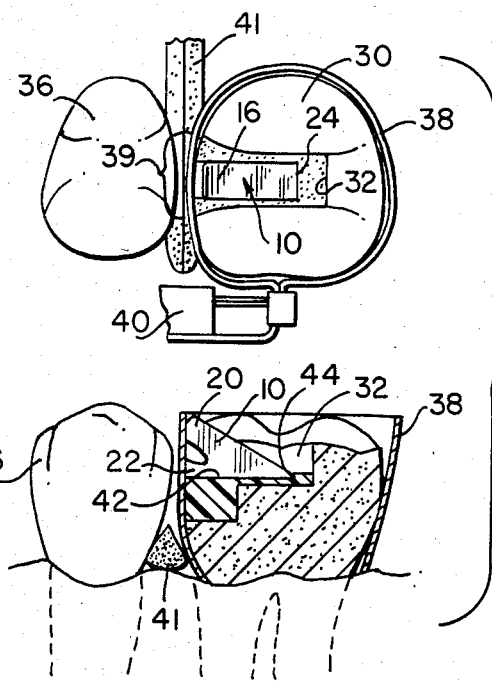
FIG. 6 is a subject matter illustrated in FIGS. 4 and 5 during one stage of the tooth restoration method of the present invention.
Figure 7:
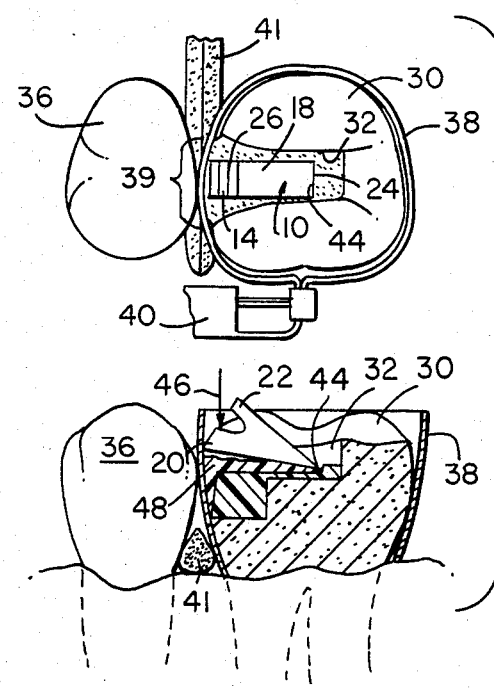
FIG. 7 is a view similar to FIG. 7 showing a more advanced stage of the restoration.
Figure 8:
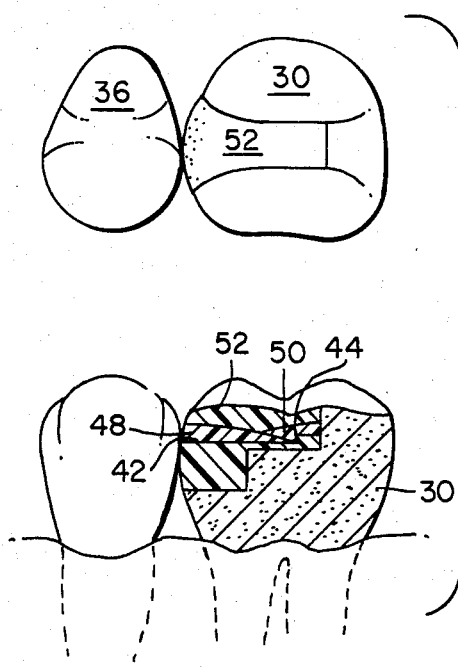
FIG. 8 is a similar combined view illustrating the completely restored tooth.

In accordance with the present invention, the flattened portion 39 of the matrix band 38 is effectively deflected outwardly toward the adjacent tooth 36 by using light curable polymeric restorative compositions in conjunction with the block 10. Thus, in FIG. 6 of the drawings the lower portion of the cavitation 32 is conventionally filled with light curable polymeric composition, usually in successively deposited and cured layers, up to a level 42 near but preferably slightly below the plane of the maximum peripheral dimension of the tooth 30 to be restored. After the material has been cured to the level 42, the block 10 is inserted into the cavitation 32 with the short arm 22 placed on the top of the previously cured polymer and with the abutment face 26 of the short arm 22 positioned against the flattened portion 39 of the matrix band 38. While so positioned, a small portion of the light curable polymer is placed about the pointed edge 24 of the block 10 and cured to establish a stepped ledge 44 in the cured partial filling. The procedure to this point is illustrated in FIG. 6.

Having formed the stepped ledge 44 in the partial cured filling, the block 10 is removed from the cavitation 32 and reinserted with the relatively long arm 20 thereof positioned downwardly and with the pointed edge 24 thereof nested pivotally against the step 44. Because of the longer length of the arm 20, the rounded end or camming surface 28 thereof will engage the inner surface of the matrix band portion 39 spanning the vertical mouth of the cavitation 32 and prevent movement of the block against the previously formed filling surface 42. A downward force exerted by a packing tool, for example, in the notch 14 of the block 10, such as a force represented by the arrow 46 in FIG. 7, will cause the end surface 28 of the block 10 to cam the matrix band portion 39 outwardly toward and preferably into contact with the adjacent tooth 36 from which the tooth 30 was deflected by the toothpick or shim 41. While the matrix band portion 39 is retained in this outwardly deformed condition by the block 10, an additional layer 48 of light curable polymer is placed into the cavitation 32 about the block 10 and cured. One or more layers like the layer 48 may be successively deposited and cured and, once so cured, will retain the matrix band 38 in the configuration to which it has been forced using the block 10. After the level of proximal contact has been exceeded by filling in this manner, the block 10 is removed and the remainder of the cavitation filled with successive layers 50 and 52, for example. When the cavitation 32 has been completely filled with cured polymer restorative, the matrix band 38 and shim 41 are removed and the surfaces of the cured polymer finished in conventional fashion. As may be appreciated in FIG. 8, proximal contact of the restored molar 30 with the adjacent tooth 36 is accomplished to substantially the same degree as prior techniques using compactable metal amalgams.

The restoration method described above has been practiced effectively with commercially available, light curable polymeric restorative compositions using various shapes and sizes of blocks like the block 10 and which were machined by hand from a sheet of plexiglass. Such handmachined models of the block 10 were dimensioned so that the shorter of the two arms, or the arm 22 in the described embodiment, approximated 5 millimeters in length whereas the longer arm 20 approximated 6 millimeters in length. The side elevational configuration of the block thus approached a 30/60 degree right triangle. Also it was found that the final shape of the block 10 could be modified by grinding or cutting a previously formed block to fit the size and shape of a particular cavitation to be filled.

It is contemplated that in production, the blocks 10 will be molded from a transparent plastic material such as polycarbonate plastic in an assortment of specific sizes. Thus, by selection of an appropriate size a minimal amount of hand tailoring will be required.

Figure 2:
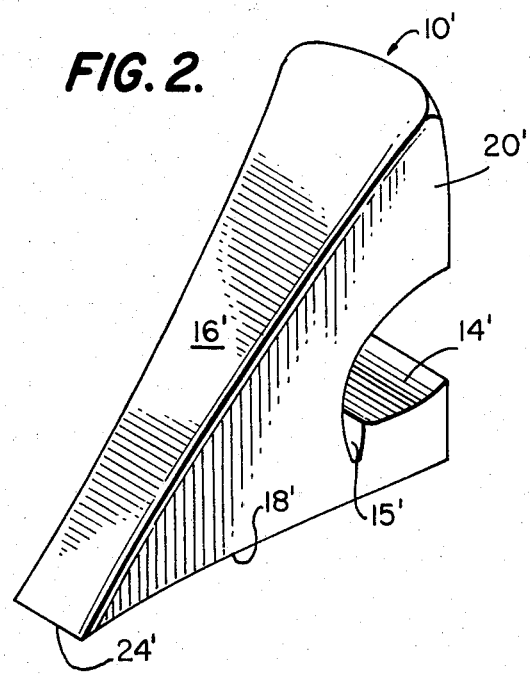
FIG. 2 is a similar view illustrating a modified shape of the device illustrated in FIG. 1.
Figure 3:
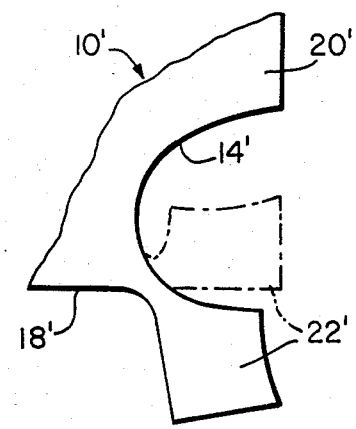
FIG. 3 is a fragmentary side elevation illustrating a provision for tweezer handling of the device illustrated in FIG. 2.
Figure 4:
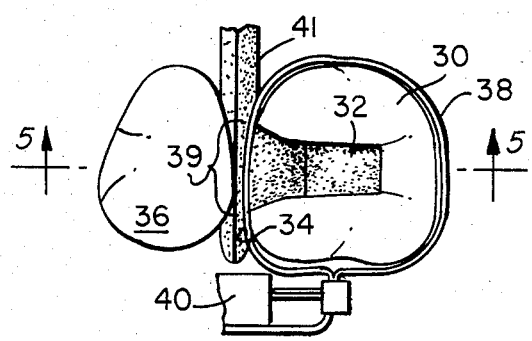
FIG. 4 is a plan view illustrating a cavitated tooth about which a matrix band has been tightened, the tooth being separated from an adjacent tooth by a pry.
Figure 5:
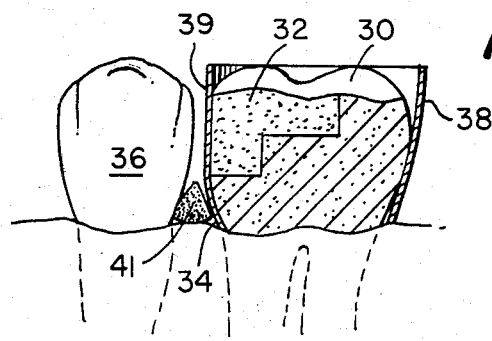
FIG. 5 is a fragmentary cross section on line 5—5 of FIG. 4.

Although the block 10 illustrated in FIGS. 1 and 1A is of uniform width throughout the length thereof as described, the shape of the block 10 may be modified to conform with the embodiment illustrated in FIGS. 2 and 3 of the drawings in which parts previously identified are designated by the same reference numeral but primed. Thus a block 10' is illustrated in FIG. 2 which generally resembles the embodiment of FIGS. 1 and 1A except that the pointed edge 24' has been reduced in width and the thickness of the block 10' flared rearwardly so that the edge 12' is substantially wider than the pointed edge 24'. This configuration facilitates the deposition of uncured polymeric restorative material about the block 10' without detracting in any way from its effectiveness to cam the matrix band outwardly as described above. An additional feature embodied in the block 10' is that the notch 14' is provided with an interior groove 15' extending toward the longitudinal surface 18' of the short arm 22'. As a result of this configuration of the notch 14', a portion of the arm 22' adjacent the notch 14' may be hinged as depicted in FIG. 3. The hinged portion of the short arm 22' may be used to handle the block 10' with tweezers, for example, when the long arm 20' is deployed as a camming strut in a cavitation to be filled.

Regardless of the particular shape of the block 10 or 10', the relative lengths $L_1$ and $L_2$ of the two arms 20 and 22 greatly contributes to the use of the block. The shorter arm functions in the manner of a gauge block to establish the position of the stepped pivot ledge against which the pointed edge 24 or 24' may be placed for use of the longer arm 20 or 20' in camming a matrix band outwardly.

Thus it will be appreciated that as a result of the present invention, a highly effective method and apparatus is provided for restoration of teeth using curable polymeric restorative compositions and by which the principle objective among others is completely fulfilled. It will be also appreciated by those skilled in the art from the preceeding description and accompanying drawings that modifications and/or changes may be made in the illustrated embodiments without departure from the invention. Accordingly, it is expressly intended that the foregoing description is illustrative of preferred embodiments only, not limiting, and that the true spirit and scope of the present invention be determined by reference to the appended claims.

I claim:

1. A device for expanding a matrix band outwardly from a vertical opening of a tooth cavitation during filling of the cavitation with light curable plastic restorative compositions, said device comprising:
   means including opposed surfaces intersecting each other at an acute angle for defining first and second arms converging at a pointed edge providing a common end for both said arms;
   means for defining an abutment surface at the end of said first arm opposite from said pointed edge; and
   means for defining a camming surface at the end of said second arm opposite from said pointed edge, the length of said second arm between said pointed edge and said camming surface being greater by a predetermined increment of length than the length of said first arm between said pointed edge and said abutment surface;
   whereby placement of said first arm in the tooth cavitation with said abutment surface against the matrix band positions said pointed edge at the location of a pivot step from which said second arm, when positioned in the cavitation with said camming surface against the matrix band, may operate as a camming strut to force the matrix band outwardly.

2. The device recited in claim 1, wherein said defining means comprise a block of generally right triangular configuration, said opposed surfaces being the edges of said block corresponding to the hypotenuse and the longer of two legs of said triangular configuration, said abutment and said camming surfaces being positioned along the shorter of said two legs.

3. The device recited in claim 2, wherein said block is formed of light transmissive material.

4. The device recited in claim 3, wherein said block is formed of polycarbonate.

5. The device recited in claim 2, wherein the shorter of said two legs of the triangular configuration is notched to separate the ends of said arms opposite from said pointed edge.

6. A device as recited in claim 5, wherein said notch is shaped to provide a necked down portion in said first arm so that the end of said first arm near said abutment surface may be hinged outwardly to provide a handle for manipulation of the device during use as a camming strut.

7. A device as recited in claim 2, wherein said block is flared outwardly so that the width of said pointed edge is narrower than the width of said block along the shorter of said two legs of the triangular configuration.

8. The method of restoring a tooth having a cavitation opening through a vertical surface of the tooth by filling the cavitation with a curable plastic restorative composition, said method comprising the steps of:

tightening a matrix band about the tooth to dam the vertical mouth of the cavitation with a flattened portion of the matrix band;

filling the cavitation with cured restorative composition to a level approximating the plane of the maximum peripheral dimension of the tooth;

building a stepped ledge of cured restorative composition at said level and spaced from the flattened portion of said matrix band;

inserting a camming strut between said stepped ledge and said flattened portion of said matrix band;

forcing said strut downwardly to cam said flattened portion of said matrix band outwardly;

depositing uncured restorative composition under said strut and against said matrix band to a level above the plane of the maximum peripheral dimension of the tooth;

curing said deposited restorative composition with said strut in place;

removing said strut from the cavitation and filling the remainder of said cavitation while said matrix band is retained by the previously deposited and cured restorative composition.

* * * * *